United States Patent [19]

Mori

[11] Patent Number: 4,796,967

[45] Date of Patent: Jan. 10, 1989

[54] SOLAR RAY ENERGY RADIATION DEVICE FOR USE IN MEDICAL TREATMENT

[76] Inventor: Kei Mori, 3-16-3-501, Kaminoge, Setagaya-Ku, Tokyo, Japan

[21] Appl. No.: 2,099

[22] Filed: Jan. 12, 1987

[30] Foreign Application Priority Data

Jan. 16, 1986 [JP] Japan ................................ 61-6972

[51] Int. Cl.⁴ .............................................. A61N 5/06
[52] U.S. Cl. .............................. 350/96.10; 128/395; 128/398; 350/108; 350/574; 350/577
[58] Field of Search .................. 350/96.10, 574, 577, 350/108; 128/362, 395, 397, 398, 396

[56] References Cited

U.S. PATENT DOCUMENTS 1,137,393  4/1915  Fogg .............................. 350/245 X
4,660,925  4/1987  McCaughan, Jr. ............. 350/96.15

*Primary Examiner*—John D. Lee
*Attorney, Agent, or Firm*—Jordan and Hamburg

[57] ABSTRACT

A solar ray energy radiation device for use in medical treatment comprises a transparent or semi-transparent cylindrical member, a cover member for closing off one end surface of the cylindrical member, and an optical conductor cable having a light ray emitting end placed on the central portion of the cover member. The solar ray energy transmitted through the optical conductor cable is radiated from the light ray emitting end into the cylindrical member. An open-ended side of the cylindrical member faces a medical treatment area. A part of the inner circumferential surface of the cylindrical member, on which the blue-colored visible light ray components of the light rays emitted from the optical conductor cable impinge, has a reflection surface provided on a ring-like shape or a ring-shaped member which is slidably disposed on the outer circumferential portion of the cylindrical member, the ring shaped member having an inner or outer circumferential surface formed as a reflection surface.

9 Claims, 2 Drawing Sheets

SOLAR RAY ENERGY RADIATION DEVICE FOR USE IN MEDICAL TREATMENT

BACKGROUND OF THE INVENTION

The present invention relates to a solar ray energy radiation device for use in medical treatment, in particular, a light ray radiation device which radiates light ray energy that corresponds to the visible light ray components of solar rays. These light rays are directed to a diseased part or a desired portion of a patient's body as a form of medical treatment; or are radiated onto the surface of a person's skin as a form of beauty treatment or for the promotion a person's general health.

In recent years, a large number of persons suffer from incurable diseases such as arthritis, neuralgia and rheumatism, or from pain caused by an injury, a bone fracture or pain from an unknown cause. Furthermore, persons cannot avoid having their skin show signs of aging which progresses gradually from a comparatively young age. On the other hand, the present applicant has previously proposed focusing solar rays or artificial light rays by the use of lenses or the like, and to guide the same into an optical conductor, then to transmit them onto an optical desired place through the optical conductor. Those light rays transmitted in such a way are employed for use in illumination or for other like purposes, as for example, to cultivate plants, chlorella, or the like. In such a process, visible light rays not containing harmful ultraviolet or infrared rays, promote health and also prevent a person's skin from aging. Furthermore, the effects of those visible light rays are very noticeable in giving patient's relief from arthritis, neuralgia, bedsores, rheumatism, injuries, bone fractures, or the like, as well as for alleviating pain from those same diseases. Such results have been corroborated by the present applicant's own experience.

On the basis of the afore-mentioned discovery, the present applicant has previously proposed in various ways a light ray radiation device for use in medical treatment capable of radiating the light rays that correspond to the visible light ray components of solar rays but not containing therein harmful components such as ultraviolet rays and infrared rays.

The light rays emitted from the optical conductor cable are discharged with an angle 46° corresponding to N.A (numerical aperture) of the optical conductor cable. On that occasion, however, the light rays of blue-colored wavelength concentrate on the outer circumferential portion by virtue of chromatic aberration, and thereby a uniform component of light rays cannot be radiated over the entire portion to be radiated so that medical treatment cannot be performed effectively.

SUMMARY OF THE INVENTION

It is an object of the present invention to provide a solar ray energy radiation device for use in medical treatment capable of effectively returning the blue-colored light rays distributed in a outer circumferential portion to the central portion.

It is another object of the present invention to provide a solar ray energy radiation device for use in medical treatment capable of radiating the light rays of a uniform quality over the entire portion to be radiated.

It is another object of the present invention to provide a solar ray energy radiation device for use in medical treatment capable of effectively radiating light ray energy of a uniform component almost corresponding to the visible light ray components of solar rays onto the diseased part or the desired portion of the patient.

The above-mentioned features and other advantages of the present invention will be apparent from the following detailed description which goes with the accompanying drawings.

DESCRIPTION OF THE PREFERRED EMBODIMENTS

Figure 1:
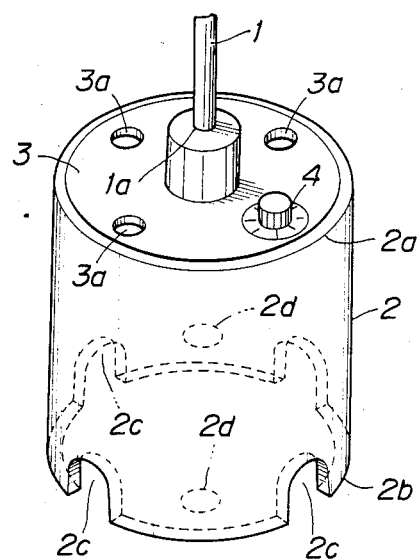
FIGS. 1 and 2 are, respectively, perspective views for explaining embodiments of a solar ray energy radiation device for use in medical treatment previously proposed by the present applicant.

FIG. 1 is a construction view for explaining an embodiment of a light ray radiation device for use in medical treatment according to the present invention. In FIG. 1, 1 is an optical conductor cable. Solar rays or artificial light rays are guided into the optical conductor cable 1 from the end portion thereof and transmitted therethrough. The light rays (the white-colored light rays) corresponding to the visible light ray components of solar rays are transmitted through an optical conductor cable 1 in such a manner as was previously proposed in various ways by the present applicant. 2 is a semi-transparent or transparent cylindrical member attached to the optical conductor cable 1 at the light ray emitting side 1a thereof, and 3 is a cover member for closing off one end 2a of the cylindrical member 2. The light ray emitting end 1a of the optical conductor cable 1 is placed at approximately the central portion of the cover member 3. Solar ray energy transmitted through the optical conductor cable 1 is channeled into the cylindrical member 2.

At the time of its use for medical treatment, another end 2b of the cylindrical member 2 is brought in line with the position for medical treatment or placed opposite the same at a desired distance. The light rays, consisting of visible light rays, transmitted through the optical conductor cable 1, as mentioned before, are focused onto a diseased part, a desired portion of a patient's body, or other various parts of the human body. As mentioned above, the light rays to be radiated onto a diseased part of a patient are light rays corresponding to the visible light ray components of solar rays which contain neither ultraviolet nor infrared rays. Thereby, it is possible to administer medical treatment without the patient suffering from any harmful effects of ultraviolet or infrared rays.

With respect to the above-mentioned light ray radiation device for use in medical treatment, since the cylindrical body 2 is constructed of a semi-transparent or transparent substance, the position of the light rays being radiated and the approximate intensity of the light rays can be assured by observing both of them with the naked eye. However, in the case of bringing the end portion 2b of the cylindrical member 2 into close contact with the diseased area or a desired portion of a patient, there is a fear that the inner wall of the cylindrical member 2 will become fogged up as a result of moisture in the form of vapor or sweat being discharged from the patient's skin, or the like, and thereby causing the interior of the cylindrical member 2 not to be visible from the outside. Furthermore, the patient's skin will not be able to breathe because the interior of the cylindrical member 2 will be filled with moisture.

In order to solve such a problem, in the case of the embodiment shown in FIG. 1, notches 2c are formed at the end portion side 2b of the cylindrical member 2 or through-holes 2d are formed on the side wall of the cylindrical member 2 so as to pass therethrough, and further, through-holes 3a are formed on the cover member 3. In such a construction, air can flow freely into the cylindrical member 2, and therefore it will be possible to prevent the interior of the cylindrical member 2 from becoming fogged up or from being filled with moisture.

Furthermore, in the case of administering medical treatment by radiating solar ray energy onto the diseased part or the desired portion of a patient as mentioned above, the time period of radiation will differ according to the condition of the patient. It is troublesome to keep watch on the radiation time period. A timer 4 is employed for setting the above-mentioned radiation time period. The time period to be set is recorded on a card or the like not shown in FIG. 1. For example, it is recorded thereon for every phase of the diseased condition. By referring to the card, the patient can set the radiation time period needed. When the timer 4 measures (counts) the set time period, it sends out an alarm sound or turns on a lamp for informing the patient that the set time period has elapsed.

Figure 2:
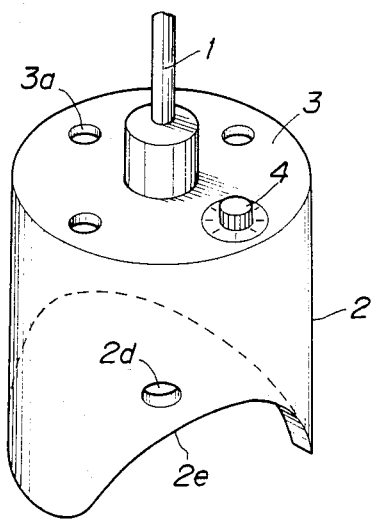

FIG. 2 is a construction view for explaining the other embodiment of a solar ray energy radiation device which has been previously proposed by the present applicant. In this embodiment, the end portion 2b of the cylindrical member 2 is formed in a shape 2e corresponding to that of a limited portion, upon which solar ray energy is administered. In the case of the embodiment shown in FIG. 2, the shape 2e is so formed that the diameter thereof coincides with that of the arm or the leg of a person. Thereby, it is possible to apply solar ray energy effectively onto the uneven skin surface of a person, namely, to radiate the same onto the diseased part of such skin surface without allowing the solar ray energy to leak outside of the device. Moreover, in FIG. 2, the parts performing the same action as that in the embodiment shown in FIG. 1 are represented by the same reference numerals.

Figure 5:
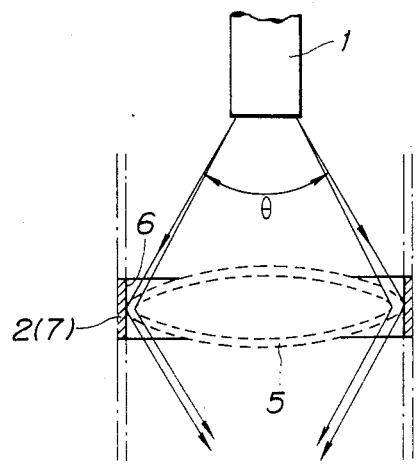
FIG. 5 is a view for explaining the operational principle of the present invention.

FIG. 5 is a view showing a state of the light rays radiated from the optical conductor cable 1 shown in FIG. 1 or FIG. 2. The light rays emitted from the optical conductor cable 1 are discharged with an angle $\theta$ (about 46°) corresponding to the N.A (numerical aperture) of the optical conductor cable 1. On that occasion, however, the light rays of blue-colored wavelength concentrate on the outer circumferential portion 5 by virtue of chromatic aberration, and thereby a uniform component of light rays cannot be radiated over the entire portion to be radiated so that medical treatment cannot be performed effectively.

The present invention was made in consideration of the actual circumstances as mentioned above, in particular, it the main object of the present invention to effectively return the blue-colored light rays distributed in the outer circumferential portion as mentioned above to the central portion and thereby to radiate light rays of a uniform quality over the entire portion to be radiated.

Figure 3:
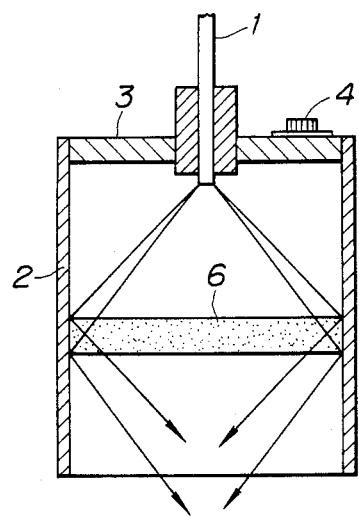
FIGS. 3 and 4 are, respectively, cross-sectional and perspective views for explaining embodiments of a solar ray energy radiation device for use in medical treatment according to the present invention.
Figure 4:
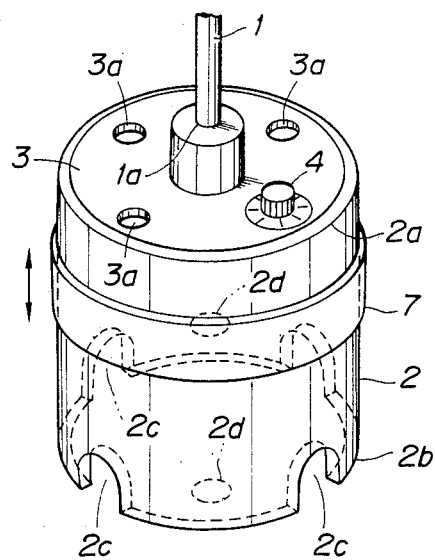

FIGS. 3 and 4 are, respectively, cross-sectional and perspective views for explaining embodiments of a solar ray energy radiation device for use in medical treatment according to the present invention. In FIGS. 3 and 4, the portions performing the same action as that of the solar ray energy radiation device for use in medical treatment shown in FIGS. 1 and 2 are represented by the same reference numerals as that of FIGS. 1 and 2.

In the embodiment shown in FIG. 3, a ring-shaped reflection surface 6 is formed in the area on which the blue-colored visible light ray component of the light rays emitted from the optical conductor cable 1 impinge on the inner circumferential surface of the cylindrical member 2 shown in FIG. 1 or 2.

In the embodiment shown in FIG. 4, a ring-shaped member 7 is mounted around the outer circumferential portion of the cylindrical member 2, and the ring-shaped member 7 can slide in the direction shown by the arrow along the outer circumferential portion of the same. A reflection surface as mentioned before is formed on the inner or outer surface of the ring-shaped member 7. By sliding the ring-shaped member 7 in the arrow direction, a predetermined position is selected in order to reflect thereon the blue-colored visible light rays component as mentioned before.

FIG. 5 shows the blue-colored visible light ray component reflected on the above-mentioned reflection surface 6. The blue-colored visible light ray component is reflected on the reflection surface of the cylindrical member 2 or on that of the ring-shaped member 7 and returned back to the position of the central portion.

As is apparent from the foregoing description, according to the present invention, it is possible to provide a solar ray energy radiation device for use in medical treatment capable of effectively radiating light ray energy of a uniform component almost corresponding to the visible light ray components of solar rays onto the diseased part or the desired portion of the patient.

I claim:

1. A solar-ray energy radiation device for the uniform application of solar rays to a localized part of a person's body comprising a cylindrical means having a cylindrical member with a longitudinal axis and a closure part on one longitudinal end of said cylindrical member, said cylindrical member being made of a transparent or a semi-transparent material, an optical conductor having a light-rays emitting end mounted on said closure part at a position generally aligned with the axis of said cylindrical member such that light rays emitted from said light-rays emitting end of said optical conductor pass into said cylindrical member, said cylindrical member confining the light rays emitted from said light-rays emitting end within said cylindrical member, said light-rays emitting end emitting the blue-colored light ray component of said light rays outwardly toward the cylindrical wall of said cylindrical member, said light rays emitted from said light-rays emitting end being emitted at an angle corresponding to the numerical aperture of said optical conductor such that said blue-colored wave length component of said light rays is concentrated on a cylindrical section of said cylindrical member as a result of chromatic aberration, the other longitudinal end of said cylindrical member being open and being adopted to face a part of a person's body to thereby radiate said light rays onto said person's body part, and return means on said cylindrical member operable to return said blue-colored light-ray component generally inwardly toward a central portion of said cylindrical member and onto said person's body part, said return means comprising a cylindrical reflection part disposed at said circumferential section of said cylindrical member, whereby light rays pass from said light-emitting end through the interior of said cylindrical member and are uniformly radiated onto said person's body part facing said open ends of said cylindrical member.

2. A solar-ray energy radiation device according to claim 1 wherein said return means is disposed on said cylindrical member at a location on said cylindrical member where the blue-colored light-ray component emitted from said optical conductor impinges on the inner cylindrical wall of said cylindrical member.

3. A solar-ray energy radiation device for the uniform application of solar rays to a localized part of a person's body comprising a cylindrical means having a cylindrical member with a longitudinal axis and a closure part on one longitudinal end of said cylindrical member, said cylindrical member being made of a transparent or a semi-transparent material, an optical conductor having a light-rays emitting end mounted on said closure part at a position generally aligned with the axis of said cylindrical member such that light rays emitted from said light-rays emitting end of said optical conductor pass into said cylindrical member, said cylindrical member confining the light rays emitted from said light-rays emitting end within said cylindrical member, said light-rays emitting end emitting the blue-colored light-ray component of said light rays outwardly toward the cylindrical wall of said cylindrical member, the other longitudinal end of said cylindrical member being open and being adopted to face a part of a person's body to thereby radiate said light rays onto said person's body part, and return means on said cylindrical member operable to return said blue-colored light-ray component generally inwardly toward a central portion of said cylindrical member and onto said person's body part, said return means comprising a cylindrical reflector part on said cylinder member, said cylinder reflector part having a cylindrical reflector surface for reflecting said blue-colored light-ray component generally radially inwardly and longitudinally toward said open end of said cylindrical member onto said person's body part facing said open end of said cylindrical member, whereby light rays pass from said light-emitting end through the interior of said cylindrical member and are uniformly radiated onto said person's body part facing said open ends of said cylindrical member.

4. A solar-ray energy radiation device according to claim 3 wherein said cylindrical reflector part is a ring-shaped member mounted on said cylindrical member.

5. A solar-ray energy radiation device according to claim 4 wherein said ring-shaped reflector part is mounted on the outside of said cylindrical member.

6. A solar-ray energy radiation device according to claim 4 wherein said ring-shaped reflector member is slidably mounted on the outside of said cylindrical member for sliding movement parallel to the longitudinal axis of said cylindrical member.

7. A solar-ray energy radiation device according to claim 4 wherein said ring-shaped reflector part has an inner cylindrical reflection surface.

8. A solar-ray energy radiation device according to claim 4 wherein said ring-shaped cylindrical part has an outer cylindrical reflection surface.

9. A solar-ray energy radiation device for the uniform application of solar rays to a localized part of a person's body comprising a cylindrical means having a cylindrical part with a longitudinal axis and a closure part on one longitudinal end of said cylindrical member, said cylindrical member being made of a transparent or a semi-transparent material, an optical conductor having a light-rays emitting end mounted on said closure part at a position generally aligned with the axis of said cylindrical member such that light-rays emitted from said light-rays emitting end of said optical conductor pass into said cylindrical member, said cylindrical member confining the light-rays emitted from said light-rays emitting end within said cylindrical member, said light rays-emitting end emitting the blue-colored light ray component of said light-rays onto said cylindrical member, the other longitudinal end of said cylindrical member being open and being adopted to face a part of a person's body to thereby radiate said light rays onto said person's body part, and a ring-shaped cylindrical part slidably disposed on the outer cylindrical surface of said cylindrical member, said ring-shaped cylindrical part having a reflecting surface for reflecting the blue-colored light-ray component generally radially inwardly and longitudinally toward said open end of said cylindrical member, whereby light-rays pass from said light-emitting end through the interior of said cylindrical member and are uniformly radiated onto said localized part of a person's body without leaking outside of said cylindrical member.

* * * * *